United States Patent [19]

Marsboom

[11] 4,005,211
[45] Jan. 25, 1977

[54] LACTATION STIMULATION EMPLOYING PIMOZIDE
[75] Inventor: Robert P. H. M. Marsboom, Vosselaar, Belgium
[73] Assignee: Janssen Pharmaceutica N.V., Beerse, Belgium
[22] Filed: Sept. 10, 1975
[21] Appl. No.: 611,940
[52] U.S. Cl. .............................................. 424/267
[51] Int. Cl.² .................................... A61K 31/445
[58] Field of Search ...................... 260/294, 293.6; 424/267

[56] References Cited
UNITED STATES PATENTS
3,196,157   7/1965   Janssen et al. ................ 260/293.6

OTHER PUBLICATIONS
Chemical Abstracts, vol. 66 (1967), p. 115709t.

Primary Examiner—V. D. Turner
Attorney, Agent, or Firm—Salvatore R. Conte

[57] ABSTRACT

Agalactia and associated disease problems have been recognized as major causes of economic loss in animal breeding, especially in such areas as swine raising. Nevertheless its importance in other fields, such as the breeding of horses, cows, sheep and dogs may not be underestimated. The loss is primarily manifested as stunting and mortality of young animals during the postnatal period. It is clear that virtually all losses attributed to starvation and many of the losses attributed to trauma, diarrhea and weakness are closely linked to insufficient milk consumption during the immediate postpartum period.

2 Claims, No Drawings

LACTATION STIMULATION EMPLOYING PIMOZIDE

DESCRIPTION OF THE INVENTION

Agalactia and associated disease problems have been recognized as major causes of economic loss in animal breeding, especially in such areas as swine raising. Nevertheless its importance in other fields, such as the breeding of horses, cows, sheep and dogs may not be underestimated. The loss is primarily manifested as stunting and mortality of young animals during the postnatal period. It is clear that virtually all losses attributed to starvation and many of the losses attributed to trauma, diarrhea and weakness are closely linked to insufficient milk consumption during the immediate postpartum period.

It has now been found that agalactia and hypogalactia in mammals, especially in sows, may successfully be prevented and treated by systemically administering to the animal an effective lactation stimulating amount of 1-{1-[4,4-bis(4-fluorophenyl)butyl]-4-piperidinyl}-1,3-dihydro-2H-benzimidazol-2-one, generically known as pimozide, or a pharmaceutically acceptable acid addition salt thereof, said pimozide and its salts being described in U.S. Pat. No. 3,196,157.

In a blind study carried out using a group of 254 sows, pimozide was administered orally by adding to the feed a granulate having the following composition:

pimozide : 0.005 g
lactose : 6.995 g
mais starch : 2.500 g
gum arabic : 0.500 g.

Animals which were given placebo received the same composition except pimozide. Prophylactic treatment with pimozide or with placebo was given in 2 or 4 consecutive feedings immediately after farrowing. Therapeutic treatment was given in 2 or 4 consecutive feedings after the symptoms of agalactia or hypogalactia became manifest. Of the total group, 60 sows received 2 oral doses of 5 mg pimozide and 63 received 4 oral doses of 5 mg pimozide prophylactically while 131 sows received placebo.

The outstanding activity of pimozide in the prevention of agalactia and hypogalactia is clearly demonstrated by the results of this trial, which are presented in the following table.

Table I

| Prophylactic activity of pimozide against agalactia and hypogalactia in sows. | | |
|---|---|---|
| Number of sows | Treatment (oral) | Number of sows showing agalactia or hypogalactia after treatment |
| 60 | 2 × 5 mg | 1 |
| 63 | 4 × 5 mg | 5 |
| 131 | placebo | 48 |

Forty-two of the 48 sows which showed agalactia or hypogalactia after administration of placebo where thereafter therapeutically treated with pimozide (2 × 5 mg or 4 × 5 mg), and the other 6 sows were treated again with placebo in order to investigate the therapeutic effect of pimozide on agalactia and hypogalactia. The results of this trial are given in the following table.

Table II

| Therapeutic activity of pimozide against agalactia and hypogalactia in sows. | | | |
|---|---|---|---|
| Number of sows | Treatment (oral) | Cured | Not cured |
| 2 | 2 × 5 mg | 0 | 2 |
| 40 | 4 × 5 mg | 39 | 1 |
| 6 | placebo | 0 | 6 |

The results obtained clearly indicate the very useful properties of pimozide as a prophylactic and therapeutic agent in the prevention and treatment of agalactia and hypogalactia. Apart from its outstanding activity in sows, it is also useful in other milk secreting animals such as, for example, dogs, cows, horses, sheep, etc..

Accordingly, this invention provides a method of stimulating lactation in mammals, which comprises the systemic administration to said animals of an effective lactation stimulating amount of 1-{1-[4,4-bis(4-fluorophenyl)butyl]-4-piperidinyl}-1,3-dihydro-2H-benzimidazo(-2-one or of a therapeutically active acid addition salt thereof. Depending on different factors such as the strain and the size of the animal to be treated, its general condition and the severity of the symptoms the amount of pimozide or salt thereof to be administered may vary within rather wide limits but, in general, doses of from about 0.5 to about 50 mg and preferably from about 2 to about 10 mg calculated as equivalent free base administered once or repeatedly may advantageously be employed.

The subject compound can be used, for example, in the form of a preparation containing a lactation stimulating amount of pimozide or of a pharmaceutically acceptable acid addition salt thereof, in admixture or conjunction with a suitable organic or inorganic, solid or liquid pharmaceutical carrier, such as, for example, water, gelatine, lactose, starch, magnesium stearate, talc, vegetable oils, gums, polyalkylene glycols, etc.. The compositions are formulated by conventional methods and may be in any one of the conventional pharmaceutical forms for systemic administration, for example, for oral, parenteral and percutaneous administration, such as solutions, suspensions, emulsions, injectables, powders, granules, capsules, tablets and pellets, including unit dosage forms thereof, as well as other convenient forms which might be suitable. They may be sterilized, for example, for parenteral administration, and/or may contain assistants such as conventional excipients, preserving, stabilizing, wetting, dispersing, desintegrating or emulsifying agents, fillers, buffers, bacteriostats, bactericidal agents, sporicidal agents, thickening agents, preservatives, coloring agents etc.. They may also contain further veterinary or therapeutically active substances. The subject compound and the lactation stimulating compositions thereof may also be used as additives and premixes to animal feeds, drinking water etc..

I claim:

1. A process of stimulating lactation in milk secreting mammals which comprises the systemic administration to said mammals of an effective lactation stimulating amount of a member selected from the group consisting of 1-{1-[4,4-bis(4-fluorophenyl)butyl]-4-piperidinyl}-1,3-dihydro-2H-benzimidazol-2-one and the pharmaceutically acceptable acid addition salts thereof.

2. A process of stimulating lactation in sows which comprises the systemic administration to said sows of an effective lactation stimulating amount of a member selected from the group consisting of 1-{1-[4,4-bis(4-fluorophenyl)butyl]-4-piperidinyl}-1,3-dihydro-2H-benzimidazol-2-one and the pharmaceutically acceptable acid addition salts thereof.

* * * * *

UNITED STATES PATENT AND TRADEMARK OFFICE
CERTIFICATE OF CORRECTION

PATENT NO. : 4,005,211
DATED : January 25, 1977
INVENTOR(S) : Robert P. H. M. Marsboom It is certified that error appears in the above-identified patent and that said Letters Patent are hereby corrected as shown below:

Under ABSTRACT -- delete what is now the Abstract and insert therefor -- Stimulating action of pimozide on lactation in mammals. --.

Signed and Sealed this

Seventh Day of November 1978

[SEAL]

Attest:

RUTH C. MASON
Attesting Officer

DONALD W. BANNER
Commissioner of Patents and Trademarks